United States Patent
Belema et al.

(10) Patent No.: US 6,331,570 B1
(45) Date of Patent: Dec. 18, 2001

(54) ACTIVE ENANTIOMER OF RARγ-SPECIFIC AGONIST

(75) Inventors: Makonen Belema, New Haven; Fred C. Zusi, Hamden, both of CT (US); Kenneth M. Tramposch, Winston-Salem, NC (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/401,356

(22) Filed: Sep. 21, 1999

Related U.S. Application Data

(60) Provisional application No. 60/125,891, filed on Mar. 24, 1999, and provisional application No. 60/101,747, filed on Sep. 24, 1998.

(51) Int. Cl.⁷ .................. A61K 31/195; C07C 229/28
(52) U.S. Cl. .................................. 514/563; 562/455
(58) Field of Search ................... 562/455; 514/563

(56) References Cited

U.S. PATENT DOCUMENTS 5,624,957  4/1997  Swann et al. ............. 514/535
5,760,084 * 6/1998  Swann et al. ............. 514/563

OTHER PUBLICATIONS

Stinson, S. C. "Chiral Drugs" Chemical & Engineering News vol. 71, No. 39, pp 38–64, Sep. 1993.*
Klaholz, et al., *Nature Structural Biology*, vol. 5 (3), pp. 199–202 (Mar., 1998).

* cited by examiner

*Primary Examiner*—James O. Wilson
*Assistant Examiner*—Leigh C. Maier
(74) *Attorney, Agent, or Firm*—David M. Morse

(57) ABSTRACT

Disclosed is the (R)-enantiomer of the formula

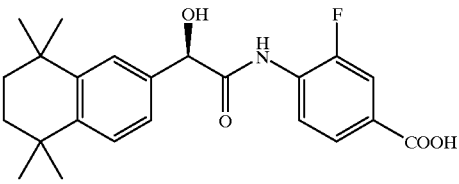

which has unexpectedly been found to possess all of the biological activity of the racemic compound disclosed in the prior art as an RARγ-specific agonist.

1 Claim, No Drawings

ACTIVE ENANTIOMER OF RARγ-SPECIFIC AGONIST

CROSS-REFERENCE TO RELATED APPLICATION

This application claims the benefit of U.S. provisional application Ser. No. 60/101,747 filed Sep. 24, 1998 and U.S. provisional application Ser. No. 60/125,891 filed Mar. 24, 1999.

BACKGROUND OF THE INVENTION

1. Field of Invention

The present invention relates to preparation of the (+) or (R)-enantiomer of an RARγ-specific agonist previously described in the prior art and the discovery that all of the retinoid activity of such agonist resided in such enantiomer.

The (R)-enantiomer of the present invention may be used in a wide variety of dermatological conditions, e.g. acne, psoriasis, eczema and photoaging of the skin, in treatment of corneopathies in opthamology, in treatment of degenerative diseases of connective tissue, e.g. arthritis, and in the treatment of malignancies.

2. Description of the Prior Art

U.S. Pat. No. 5,624,957 discloses the racemic compound, 3-fluoro-4(2'(5",6",7",8"-tetrahydro-5",5",8",8"-tetramethyl-2"-naphthyl)-2'-hydroxy)acetamidobenzoic acid (see Example 1) as an RARγ-specific retinoid with the highly useful property of lacking the liver toxicity of non-elective retinoids. The compound is also disclosed by B. P. Klaholz, et al., *Nature Structural Biology*, 5(3), pp. 199–202 (1998), as a complex with the RARγ receptor protein. However, the compound indicated as binding to the receptor is the (S)-enantiomer, which is the inactive form.

Although the above-described patent reference indicates that the disclosed RARγ-specific retinoids exist in the form of the individual enantiomers as well as racemic mixtures, there is no disclosure of the (R)-enantiomer or the fact that, unexpectedly, all of the retinoid activity of the compound of Example 1 resides in this enantiomer.

SUMMARY OF THE INVENTION

The present invention provides the compound of the formula

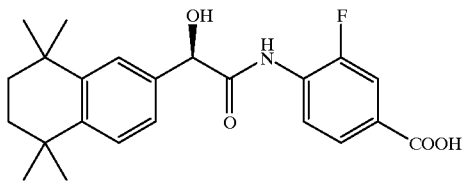

R-enantiomer or a pharmaceutically acceptable salt thereof. Enantiomer IA has retinoid-like activity and is thus useful in the treatment of skin disorders such as acne, Darier's disease, psoriasis, icthyosis, eczema, atopic dermatitis and epithelial cancers. It is also useful in the treatment of arthritic diseases and other immunological disorders (e.g. lupus erythematosus), in promoting wound healing, in treating dry eye syndrome and in treatment of the effects of sun damage to skin, i.e. photoaging. It is also useful in the treatment of various malignant tumors and premalignant skin lesions, e.g. actinic keratoses.

Also included in the invention is a process for preparing enantiomer IA via chiral synthesis or separation, and pharmaceutical compositions containing the enantiomer IA in combination with a pharmaceutically acceptable carrier or diluent.

In another aspect of the invention there is provided a method for treating a mammalian host for dermatological, rheumatic, antitumor, respiratory or opthamological conditions known to be affected by retinoid derivatives which comprises administering a therapeutically effective amount of a compound of formula IA or a pharmaceutically acceptable salt thereof.

In yet another aspect of the invention, there is provided a method for the prevention of spontaneous squamous cell carcinoma in immunocompromised human transplant patients which comprises systemically administering a therapeutically effective amount of a compound of formula IA.

DETAILED DESCRIPTION OF THE INVENTION

As noted above the racemic compound of the formula

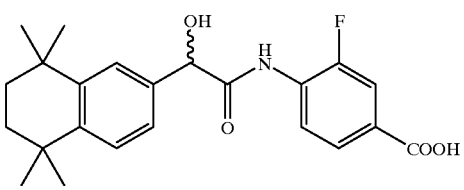

is disclosed in U.S. Pat. No. 5,624,957 along with its method of preparation and therapeutic uses. Compound I is an RARγ-specific agonist which has the advantage of lacking the liver toxicity characteristic of non-specific retinoids.

The present inventors have discovered, surprisingly and unexpectedly, that all of the retinoid activity of compound I resides in the (+) or (R)-enantiomer IA, i.e.

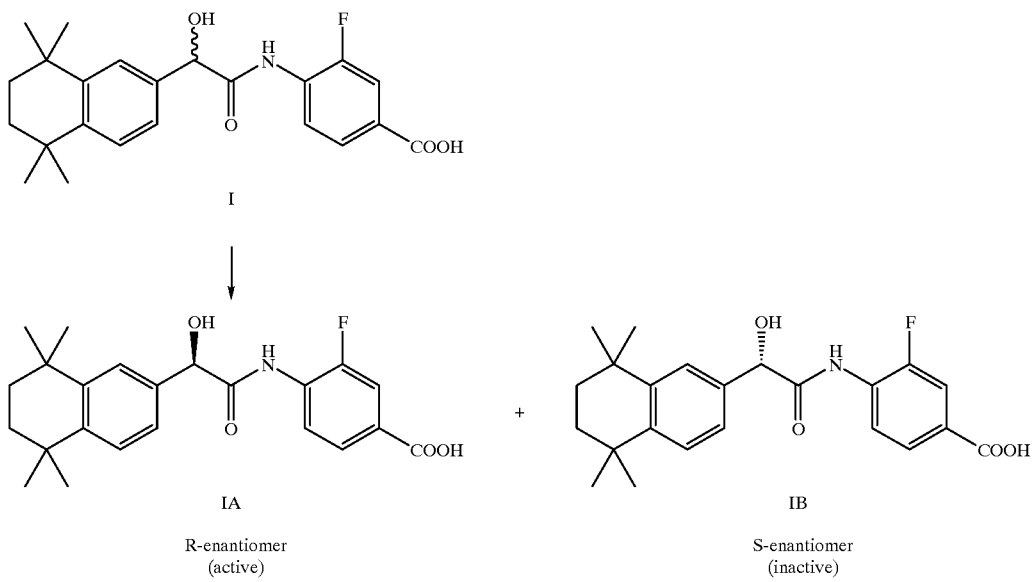

I

IA
R-enantiomer
(active)

IB
S-enantiomer
(inactive)

The individual enantiomers of compound I may be isolated by subjecting the allyl ester of compound I (6, below) to chiral chromatography to isolate the allyl esters of the enantiomeric acids, followed by cleavage under mild conditions to preserve the enantiomeric purity of the products. The synthesis of 6 generally follows the synthesis disclosed in U.S. Pat. No. 5,624,957:

Known acid 1 (U.S. Pat. No. 5,624,957) can be reduced to the amino acid, 2, using either catalytic hydrogenation or a chemical reducing agent, such as stannous chloride. Acid 2 can be converted to amino ester 3 using, for example, allyl bromide. Known acid 4 is then converted to its acid chloride and condensed with 3 to give 5, which may be reduced using sodium borohydride to give 6.

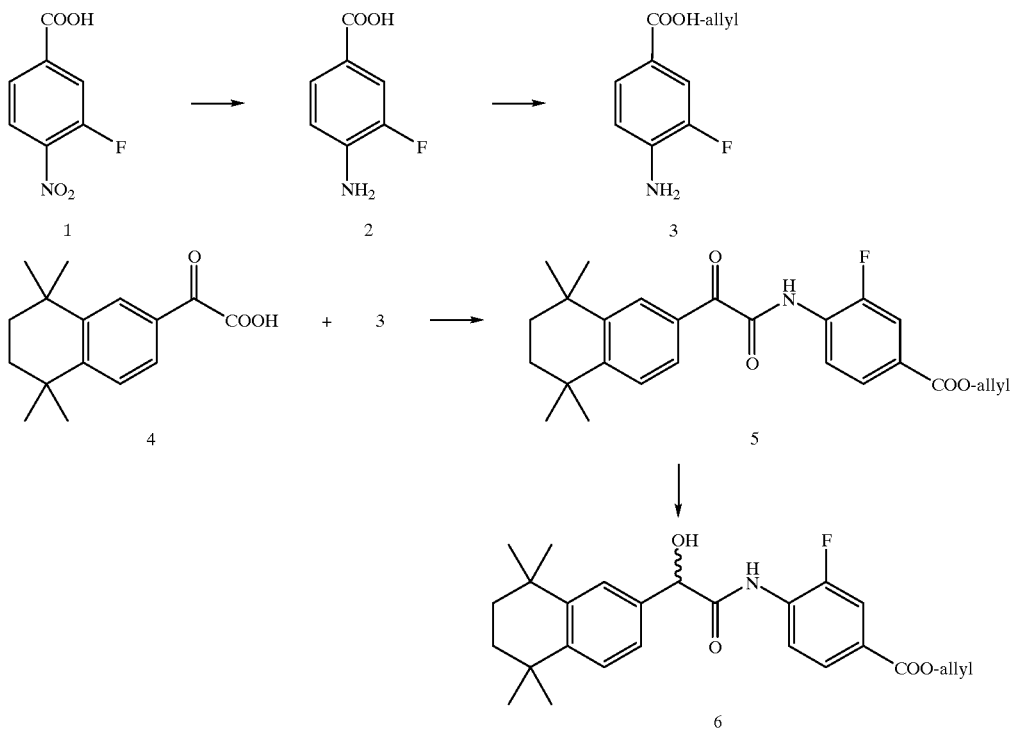

Intermediate 6 is then subjected to chromatography on a Chiralpak AD column to give 7a and 7b, which are cleaved under mild conditions (for example, morpholine and palladium catalyst) to give the individual (R) and (S) enantiomers.

The active (R) I may be enantioselectively synthesized by the following pathway, using as a key step, the enantioselective reduction of ketoester 10 with known chiral reducing agent (R)-Alpine borane:

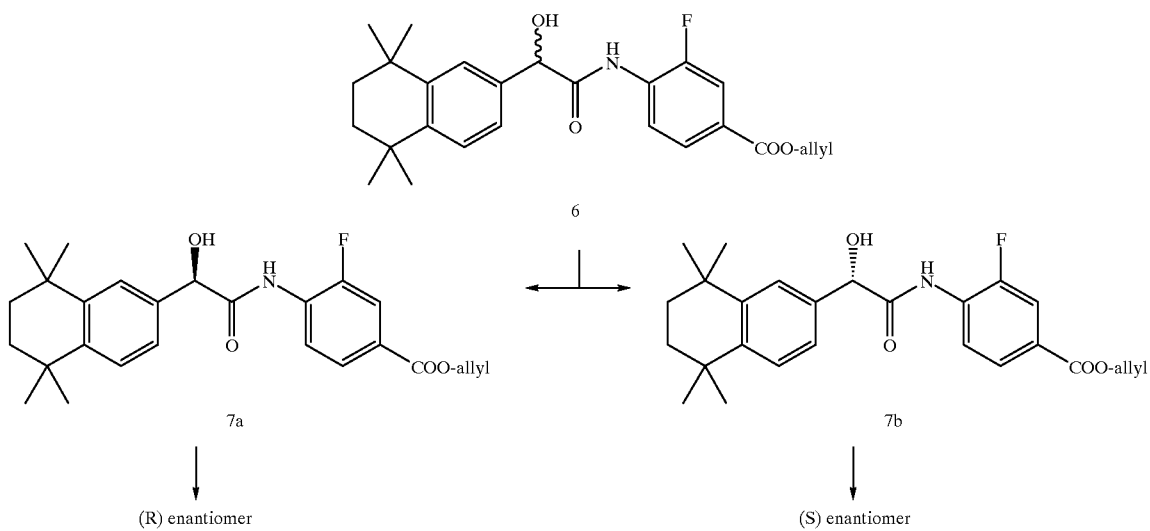

Optical purity analysis was carried out by chiral analytical HPLC, following derivatization of the free acid to the corresponding methyl ester under non-racemizing conditions. The determination of absolute configuration was carried out by X-ray crystal analysis of 8, the (R)-Mosher ester of 7a:

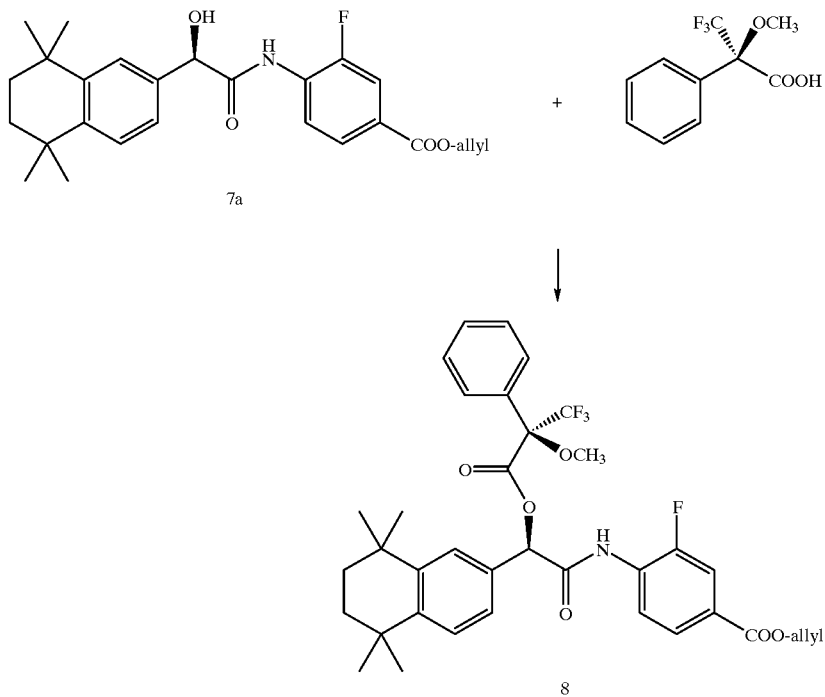

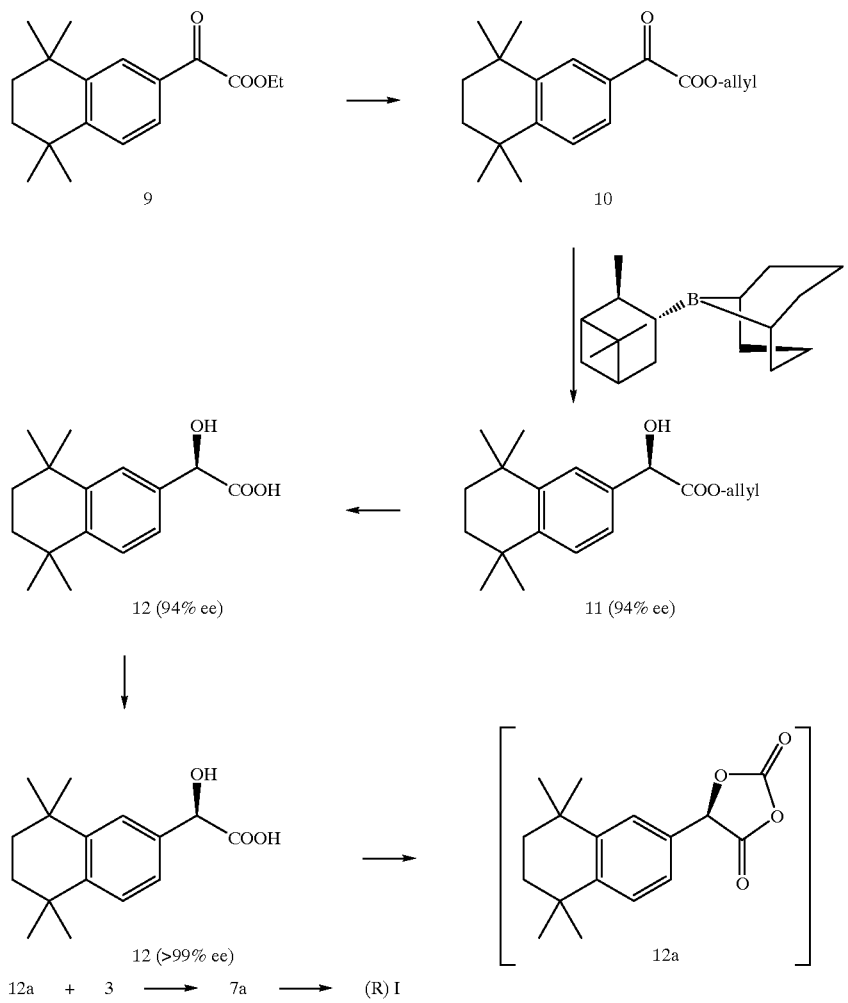

Known ethyl ester 9 (U.S. Pat. No. 5,624,957) is converted to allyl ester 10 using base hydrolysis followed by allyl bromide alkylation. 10 is then enantioselectively reduced to 11 using (R)-Alpine borane. The crude 11 (~94% ee) is hydrolyzed to crude 12 (94% ee), then 12 is purified to >9 % ee via crystallization. Activation of 12 with diphosgene and condensation with amino ester 3 gives 7a, whose ester group is cleaved to give the final product, (R) I (ee>99%).

Compound IA may be converted with bases to pharmaceutically acceptable salts thereof by methods known in the art. Examples of suitable salts are ammonium and alkali metal salts, especially of sodium, potassium and lithium, and alkaline earth metal salts, especially calcium and magnesium, as well as salts with suitable bases such as with lower alkylamines, e.g. methylamine, ethylamine or cyclohexylamine, or with substituted lower alkylamines such as diethanolamine or triethanolamine and with piperidine or morpholine.

As noted above, the compound of the present invention has retinoid-like activity and can, therefore, be used for the treatment of dermatological, rheumatic, antitumor, respiratory and opthalmological conditions know to be affected by retinoid derivatives. For example, the compound may be used for the treatment of:

dermatological conditions linked to a disorder of keratinisation involving differentiation and proliferation, e.g. in treating acne vulgaris, comedonic or polymorphic acne, nodulocystic acne, acne conglobata, senile acne and secondary acnes such as solar, drug and occupational acne;

for treating other types of keratinisation disorders such as ichthyoses, ichthyosiform states, Darier's disease, palmoplantar keratoderma, leucoplakia and leucoplakiform states, and lichenplanus;

for treating dermatolgical conditions linked to a keratinisation disorder with an inflammatory and/or immunoallergic component, e.g. all forms of psoriasis, whether cutaneous, mucosal and ungual, and psoriatic rheumatism, or alternatively, cutaneous atopy, such as eczema, or repiratory atopy;

for treating dermal or epidermal proliferations, whether benign or malignant, including those of vital origin, such as common warts, flat warts and epidermodysplasia verruciformis;

for treatment of other dermatological disorders such as vesicular dematoses and collagen diseases;

for treatment of certain opthalmological disorders: in particular corneopathies;

for prophylaxis or treatment of skin aging, both light induced (photoaging) and that occurring with the passage of time;

for preventing or treating the stigmata of epidermal and/or dermal atrophy induced by local or systemic corticosteroids, or any other form of cutaneous atrophy;

for treatment of malignant tumors;

for treatment of premalignant skin lesions such as actinic keratosis;

for rheumatic illnesses, especially those of an inflammatory or degenerative kind which attack the joints, muscles, tendons and other parts of the motor apparatus, e.g. rheumatic arthritis;

for promoting cicatrisation; and for combating disorders of sebaceous function, such as seborrhea of acne or simple seborrhea.

Skin cancers, especially squamous cell carcinomas, are the most frequent malignancies in immunocompromised patients, e.g. organ transplant recipients. Systemic retinoids such as isotretinoin have been studied for prevention of spontaneous squamous cell carcinomas, but adverse side-effects on long-term use such as liver toxicity limit their usefulness. Compound IA, however, lacking the liver toxicity of non-specific retinoids, is especially useful for this indication. Thus the present invention includes the method of preventing spontaneous squamous cell carcinomas in immunocompromised human transplant patients which comprises systemically administering a therapeutically effective amount of a compound of formula IA.

The compounds of the present invention can be administered orally, parenterally or topically, depending on such considerations as the condition to be treated, need for site-specific treatment, quantity of drug to be administered, and similar considerations. They are generally used as pharmaceutical compositions with one or more suitable pharmaceutical carriers or diluents conventionally used in pharmaceutical technology.

In the treatment of dermatological conditions, it will generally be preferred to administer the compounds topically, although in certain cases such as treatment of severe acne or psoriasis, oral formulation will be employed. For other indications, parenteral, oral or topical administration may be preferred. The pharmaceutical compositions may be in solid form such as capsules, tablets, powders, gels, salves, ointments, etc. or in liquid form such as solutions, suspensions or emulsions. For parenteral administration, the drug may be prepared in unit dose form in ampules or in multidose containers and may contain additives such as suspending, stabilizing and dispersing agents. The parenteral compositions may be in ready-to-use form or in powder form for reconstitution at the time of delivery with a suitable vehicle such as sterile water. Illustrative examples of suitable pharmaceutical formulations are disclosed, for example, in U.K. 2,164,938A.

The compound of the present invention may be administered alone or in admixture with other medicaments, e.g. agents for treating skin dryness, providing protection against photoaging, preventing infection, reducing irritation and inflammation, and the like.

The dosages and dosage regimen in which the compound of the present invention are administered will vary according to the compound, dosage form, mode of administration, the condition being treated and the particulars of the patient being treated. Accordingly, optimal therapeutic concentrations will be best determined at the time of administration by conventional dosage determination procedures. In general, however, the compounds may be administered in amounts of about 0.05 mg to about 5 mg daily per kg of body weight in one or more doses.

Isotretinoin (Accutane®) and etretinate (Tegison®) are used clinically to treat severe recalcitrant cystic acne and severe recalcitrant psoriasis, including the erythrodermica and generalized pustular types, respectively. Their mode of use is amply illustrated in the *Physician's Desk Reference*, 47th Edition (1993), published by Medical Economics Data. The compounds of the present invention may be administered in a similar fashion to isotretinoin and etretinate according to these guidelines. For treatment of other indications, such as tumors, the compounds of the present invention may be administered to mammals, including humans, in a similar manner to retinoid compounds in the literature which have been shown to be active for such indications.

DESCRIPTION OF SPECIFIC EMBODIMENTS

The specific example which follows illustrates the synthesis of the enantiomer of the present invention.

Definitions for some of the abbreviations used below are as follows:

| | |
|---|---|
| DMSO | dimethylsulfoxide |
| $CDCl_3$ | deuterated chloroform |
| EtOH | ethyl alcohol |
| DMF | dimethylformamide |
| ee | enantiomeric excess |
| EtOAc | ethyl acetate |
| $Et_3N$ | triethylamine |
| IPA | isopropyl alcohol |
| DCC | dicyclohexylcarbodiimide |
| Ph | phenyl |
| THF | tetrahydrofuran |
| TMS | trimethylsilyl |

A. 4-Amino-3-fluorobenzoic acid, 2-propenyl ester, 3

10% Pd/C (1.98 g) was added to a 450 mL hydrogenation flask, and the flask was flushed with $N_2$. A solution of nitro benzoic acid 1 (21.9 g, 118.3 mmol) in 140 mL ethanol and acetic acid (1 mL) were added to the flask. Hydrogenation was conducted at 15 psi in a carefully controlled manner, wherein after the pressure of $H_2$ drops to zero, the shaking of the flask was continued for a couple of minutes before re-pressurizing. After the hydrogen uptake ceased, the pressure was raised to 40 psi, and continued shaking for an additional 30 minutes to insure completion of the reduction. The catalyst was filtered through Celite, and solvent was removed in vacuo to afford amino benzoic acid 2 as an off-white solid.

The crude acid 2 was dissolved in DMF (140.0 mL), treated with $K_2CO_3$ (16.0 g, 115.8 mmol) and allyl bromide (11.8 mL, 132.3 mmol), and vigorously stirred at room temperature for 24 hours. The crude reaction mixture was treated with 1N HCl (120 mL) carefully. It was then diluted with water (70 mL), and extracted with $CH_2Cl_2$ (400 mL). The organic layer was washed with water (70 mL, 5×) and brine. It was dried with $MgSO_4$, filtered and evaporated in vacuo to afford a crude oil. The crude oil was purified with flash chromatography (silica gel; 10–20% EtOAc/hexanes) to afford aniline 3 as a faint yellow solid (20.4 g, combined yield).

3: Mp 53.5–55.5° C. IR (KBr): 3418, 3337, 3215,1708, 1639, 1609, 1582, 1522. $^1$H NMR (CDCl$_3$, δ=7.28): 7.73–7.68 (m, 2H, C-2H & C-6H), 6.77 (app t, J=8.6, 1H, C-5H), 6.03 (m, 1 H, OCH$_2$CH), 5.40 (dm, J=16.4, 1H, =CH$_2$ trans), 5.28 (dm, J=10.4, 1H, =CH$_2$ cis), 4.79 (dm, J=5.6, 2H, OCH$_2$), 4.21 (br s, 2H, NH$_2$). LRMS: (ESI) m/z (M–H)$^-$=194.3.

Anal. Calcd. for C$_{10}$H$_{10}$FNO$_2$: C, 61.53; H, 5.16; N 7.18. Found: C, 61.60; H, 5.18; N, 7.16.

B. 3-Fluoro-4(2'(5",6",7",8"-tetrahydro-5",5",8",8"-tetramethyl-2"-naphthyl)2'-oxo)acetamido benzoic acid, 2-propenyl ester, 5

Et$_3$N (16.0 mL, 114.8 mmol) was added over five minutes to a cooled (0° C.) CH$_2$Cl$_2$ (100.0 mL) solution of acid 4 (10.15 g, 39.00 mmol) and SOCl$_2$ (8.0 mL, 109.7 mmol). The cooling bath was removed 10 minutes later, and stirring was continued at room temperature for additional 1 hour and 50 minutes. The reaction mixture was diluted with CH$_2$Cl$_2$, and washed quickly with water and dried over MgSO$_4$. It was filtered, and solvent was removed in vacuo to afford a dark brown viscous oil, which was submitted to the coupling step without any purification.

Et$_3$N (8.0 mL, 57.4 mmol) was added drop-wise over a few minutes to an EtOAc (110.0 mL) solution of the allyl benzoate 3 (7.30 g, 37.6 mmol) and the acid chloride prepared above. It was then stirred overnight. The mixture was diluted with EtOAc, and washed with water and brine. The organic layer was dried with MgSO$_4$, filtered and evaporated in vacuo. Flash chromatography (the oil was loaded directly to silica gel; 5–7% EtOAc/hexanes) afforded ketoamide 5 as a red-brown viscous oil which eventually solidified to a dense solid. It weighed 11.38 g (a combined yield of 67%).

5: IR (KBr) 3352, 2959, 2922, 1719, 1705, 1670, 1618, 1599, 1528. $^1$H NMR (CDCl$_3$, δ=7.28) 9.42 (br s, 1 H, NH), 8.63 (app t, J=8.1, 1H, NHCCH), 8.43 (d, J=1.8, 1H, HCCCO), 8.18 (dd, J=8.4, 1.8, 1H, HCCCO), 7.96 (d, J=8.7, 1H, FCCH), 7.87 (dd, J=11.2, 1.8, 1H, NCCHCH), 7.47(d, J=8.4, 1 H, CHCHCCO), 6.05 (m, 1H, OCH$_2$CH), 5.44(dm, J=17.2, 1 H, =CH$_2$ trans), 5.34 (dm, J =10.4, 1H, =CH$_2$ cis), 4.85 (dt, J=5.7, 1.2, 2H, OCH$_2$), 1.75 (s, 4H, CH$_2$CH$_2$), 1.37(s, 6H, CH$_3$/CH$_3$), 1.34 (s, 6H, CH$_3$/CH$_3$). LRMS: (ESI) m/z (M–H)$^-$=436.4.

C. 3-Fluoro-4(2'(5",6",7",8"-tetrahydro-5",5",8",8"-tetramethyl-2"-naphthyl)2'-hydroxy)acetamido benzoic acid, 1(2-propenyl) ester, 6

NaBH$_4$ (16.5 mg, 0.436 mmol) was added in one portion to an allyl alcohol (11.0 mL) solution of ketoamide 5 (450.0 mg, 1.029 mmol). The reaction mixture was stirred vigorously for 10 minutes, then quenched with 2 drops of concentrated HCl, and partitioned between EtOAc (150 mL) and dilute NaHCO$_3$ solution (i.e., 5 mL saturated NaHCO$_3$ solution+45 mL water). The water layer was back extracted with EtOAc (50 mL). The combined organic phase was washed with brine and dried with MgSO$_4$. It was then filtered and evaporated. Flash chromatography of the crude material (sample was loaded as a silica gel mesh; 20–25% EtOAc/hexanes) afforded alcohol 6 as a colorless oil which solidified slowly at room temperature. It weighed 412 mg (yield=91.1%).

6: IR (KBr) 3600–3150 (br), 3366, 2959, 1719, 1692, 1620, 1593, 1532. $^1$H NMR (CDCl$_3$, δ=7.28) 8.75 (br s,1H, NH), 8.51 (app t, J=8.2, 1H, FCCCH), 7.88 (d, J=8.7, 1H, FCCH), 7.81 (dd, J=11.4, 1.8, 1H, NCCHCH), 7.42 (d, J=1.9, 1H, CCHCCO), 7.37 (d, J=8.2, 1H, CHCHCCHOH), 7.25 (dd, J=8.2, 1.9, 1H, CHCHCCHOH), 6.04 (m,1H, OCH$_2$CH), 5.42 (dm, J=17.2, 1H, =CH$_2$ trans), 5.32 (dm, J=11.7, 1H, O=CH$_2$ cis), 5.25 (d, J=3.0, 1H, CHOH), 4.83 (dm, J=5.7, 2H, OCH$_2$), 3.05 (d, J=3.0, 1H, OH), 1.70 (s, 4H, CH$_2$CH$_2$), 1.33 (s, 3H, CH$_3$), 1.30 (s, 3H, CH$_3$), 1.29 (s, 6H, CH$_3$/CH$_3$). LRMS: (ESI) m/z (M–H)$^-$=438.3.

D. (R) and (S)-3-Fluoro-4(2'(5",6",7",8"-tetrahydro-5",5",8",8"-tetramethyl-2"-naphthyl)2'-hydroxy) acetamido benzoic acid, 2-propenyl ester, 7a and 7b The resolution of alcohol 6 was effected on Waters HPLC system with a 4000 series system-control and a 490E series detector according to conditions described below. The elution pattern was monitored at four wavelengths (210, 254, 280 and 300 nm) where similar absorption profiles were observed.

Column: Chiralpak AD (5 cm×50 cm) pre-equilibrated with 60:40 hexanes/IPA for 0.5 hour.

Sample Loading: 3.0 g of alcohol 6 was added to 40 mL of 1:1 hexanes/IPA. The mixture was sonicated with moderate heating (~40° C.) until total dissolution was effected. The solution was removed from the sonicating bath and allowed to cool to room temperature. It was then loaded directly onto the column at 10 mL/minutes.

Elution: Elution of the column was carried out with a 60:40 hexanes/IPA solution at 50 mL/minutes. Sample collection was carried out manually in three fractions: the first enantiomer (7a) came out between 15–25 minutes; the intermediate fraction was discarded, and the last fraction was the second enantiomer (7b) which eluted between~40–65 minutes.

Removal of solvent in vacuo afforded a viscous oil, in both cases.

Analysis of Optical Purity: Both fractions were determined to be optically pure when analyzed according to the following conditions:

Instrument: HP 1090 Liquid Chromatography with DAD
Column: Chiracel AD, 0.46 cm×25 cm
Mobile Phase: 80/20 (hexanes/IPA)
Flow Rate: 1.5 mL/min
Detection: UV absorption @ 210 nm
Sample was prepared in 1:1 hexanes/IPA
Elution time: alcohol 7a (2.86 min) and alcohol 7b (10.92 min)

E. (R) 3-Fluoro-4(2'(5",6",7",8"-tetrahydro-5",5",8",8"-tetramethyl-2"-naphthyl)2'-((R)-α-methoxy-α-trifluoromethylphenylacetoxy)) acetamido benzoic acid, 2-propenyl ester, 8

DCC (115.0 mg, 0.557 mmol) was added in one portion to a CH$_2$Cl$_2$ (3.0 mL) solution of (R)-Mosher acid (127.0 mg, 0.542 mmol), alcohol 7a (197.0 mg, 0.449 mmol) and DMAP (5.2 mg, 0.043 mmol). The reaction was stirred for a total of 4 hours and filtered through a cotton plug to remove the urea byproduct. The solvent was removed in vacuo and the resulting oil was submitted to flash chromatography (silica gel; 10–15% EtOAc/hexanes) to afford Mosher ester 8 as a white foam (278 mg, 94%). X-ray quality crystals were grown in EtOH (~2 mL) with a few drops of water, at room temperature. The absolute structure of the benzylic position of 7A was determined to be (R).

F. (R) 3-Fluoro-4(2'(5",6",7",8"-tetrahydro-5",5",8",8"-tetramethyl-2"-naphthyl)2'-hydroxy)acetamido benzoic acid, (R)-IA Pd(Ph$_3$P)$_4$ (216.0 mg, 0.187 mmol) was added in one portion to a THF (50.0 mL) solution of allyl ester 7a (3.00 g, 6.826 mmol) and morpholine (5.0 mL, 57.34 mmol). The solution was stirred for 40 minutes, diluted with EtOAc (150 mL), and washed with 1N HCl (40 mL, 2×) and brine. The organic layer was dried with MgSO$_4$, filtered and evaporated in vacuo to afford a solid. The sample was purified with flash chromatography (short column; sample was loaded as a silica gel mesh; 75 hexanes: 24 EtOAc: 0.5 of 90% HCO$_2$H: 0.5 MeOH) to afford acid (R) I as a white solid weighing 2.50 g (91.6%). Recrystallization: about 8 mL of EtOAc was added to the solid, and the mixture was heated until total dissolution was effected. Upon addition of hexanes (65 mL) to the solution, white crystals started forming immediately. Half hour later, the solid was filtered and washed with 20% EtOAc/hexanes. Exposure of the sample to high vacuum afforded 1.824 g of acid.

(R) I: MP 193.0–195.5° C.

Anal. Calcd. for C$_{23}$H$_{26}$FNO$_4$: C, 69.16; H, 6.56; N, 3.51. Found: C, 69.07; H, 6.57; N, 3.31.

(S) I: MP 194.5–197° C.

Anal. Calcd. for C$_{23}$H$_{26}$FNO$_4$: C, 69.16; H, 6.56; N, 3.51. Found: C, 69.01; H, 6.51; N, 3.28.

| | Specific Rotation [MeOH, 25°] | | | |
|---|---|---|---|---|
| Wavelength | Allyl ester 7a | Allyl ester 7b | Acid (R) IA | Acid (S) IB |
| 589 nm | +2.577 | −2.476 | +1.720 | −1.630 |
| 578 nm | +3.319 | −3.461 | +2.271 | −2.390 |
| 546 nm | +5.072 | −5.399 | +3.875 | −4.235 |
| 436 nm | +22.307 | −23.525 | +21.008 | −21.855 |
| 365 nm | — | −81.153 | +77.404 | −78.629 |

Optical purity analysis of the methyl esters: Acid IA (31.4 mg, 0.0786 mmol) was dissolved in 3.0 mL of C$_6$H$_6$/MeOH (7:2) mixture, and treated with TMS-diazomethane (200 μL of 2.0 M in hexanes, 0.40 mmol). After the reaction mixture was stirred for 11 minutes, the excess reagent was quenched with 2 drops of acetic acid. Most of the volatile component was removed in vacuo, and the crude material was directly submitted to flash chromatography (silica gel; 15% EtOAc/hexanes) to afford the methyl ester of IA as a colorless oil. HPLC analysis of the ester on an AD column indicated that it was optically pure. (Elution time: (R)-methyl ester =3.00 min; (S)-methyl ester =11.17 min)

G. 2-Oxo-(5',6',7',8'-tetrahydro-5',5',8',8'-tetramethyl-napth-2'-yl)acetic acid, 2-propenyl ester, 10

A KOH solution (150.0 mL of 1.76 M, 264.0 mmol) was added to an EtOH (350 mL) solution of ethyl ketoester 9 (50.3 g, 174.4 mmol). After a thorough mixing, the solution was allowed to stand at room temperature for 30 minutes. It was diluted with water (500 mL) and acidified with 5% HCl to pH 3–4. The aqueous layer was extracted with EtOAc (1.0 L and 250 mL). The combined organic phase was washed with brine, dried with MgSO$_4$, filtered and evaporated in vacuo. The resulting crude oil was exposed to high vacuum over night to afford acid 4 as a yellow solid.

K$_2$CO$_3$ (24.0 g, 173.6 mmol) and allyl bromide (18.0 mL, 208.0 mmol) were added to a DMF (200 mL) solution of the crude acid. The allylation was complete with in 150 minutes. The reaction mixture was slowly treated with 1 N HCl (170 mL), with vigorous stirring. The resulting mixture was diluted with water (100 mL), and extracted with CH$_2$Cl$_2$ (500 and 100 mL). The combined organic phase was washed with water (100 mL, 5×), and brine, dried with MgSO4, filtered and evaporated in vacuo. The crude oil was purified with flash chromatography (silica gel; 10% EtOAc/hexanes) to afford ester 10 as a dense solid (50.0 g, 95% combined yield).

10: IR (KBr): 2963, 2930, 2869, 1736, 1682, 1600. $^1$H NMR (CDCl$_3$, δ=7.28): 8.00 (d, J=1.9, 1H, C-1H), 7.73 (dd, J=8.3, 1.9, 1H, C-3H), 7.45 (d, J=8.3, 1H, C-4H), 6.05 (m, 1H, CH=CH$_2$), 5.47 (dm, J=17.2, 1H, =CH$_2$ trans), 5.37 (dm, J=10.5, 1H, =CH$_2$ cis), 4.89 (dm, J=5.9, 1H, OCH$_2$), 1.73 (app s, 4H, CH$_2$CH$_2$), 1.324 (s, 6H, CH3/CH$_3$), 1.320 (s, 6H, CH3/CH3). LRMS: (ESI) m/z (M−H)$^-$=259.4.

Anal. Calcd. for C$_{19}$H$_{24}$O$_3$: C, 75.97; H, 8.05. Found: C, 75.92; H, 8.21.

H. (R)-2-Hydroxy-(5',6',7',8'-tetrahydro-5',5',8',8'-tetramethyl-napth-2'-yl) acetic acid, 1(2-propenyl)ester, 11

Ketoester 10 (33.60 g, 111.85 mmol) was ground up with a mortar and pestle and transferred into a 1L round-bottomed flask equipped with a magnetic stirrer. The flask was then flushed with nitrogen. (R)-Alpine-Borane (57.0 mL, 202.7 mmol; 97% neat liquid) was transferred to the reaction flask via syringe. The mixture was vigorously stirred at room temperature for a total of 64 hours.

To quench the excess Alpine-Borane, the mixture was cooled to 15° C. and treated with acetaldehyde (16.8 mL, 300.5 mmol). A few minutes later, the cooling bath was removed and the reaction mixture was stirred at room temperature for 45 minutes. The reaction mixture was then flushed with N$_2$ while being heated with a water bath of 45° C. which was allowed to cool down to room temperature over the next 3.75 hours.

Ether (200 mL) was added to the reaction mixture. The resulting solution was cooled to ~10° C. and treated with ethanol amine (14.5 mL, 240.2 mmol) drop-wise over a few minutes. The cooling bath was removed and the mixture was stirred at room temperature for an additional 30 minutes.

The mixture was filtered, and the white precipitate was washed with hexanes (140 mL). The filtrate was diluted with EtOAc (200 mL) and washed with dilute HCl solution (prepared from 200 mL water and 5 mL of 5% HCl). The organic layer was washed with brine, dried with MgSO$_4$, filtered and evaporated in vacuo to afford a semi-viscous oil.

The crude material was directly submitted to flash chromatography (silica gel; 7.5–20% EtOAc/hexanes) to afford impure hydroxy ester 11 (33.8 g) as a colorless oil.

I. (R)-2-Hydroxy-(5',6',7',8'-tetrahydro-5',5',8',8'-tetramethyl-napth-2'-yl) acetic acid, 12

Morpholine (42.0 mL, 481.6 mmol), followed by Pd(Ph$_3$P)$_4$ (1.00 g, 0.865 mmol) were added to a THF (420 mL) solution of 33.8 g impure hydroxy ester 11. The flask was flushed with N$_2$ for a few minutes, and the reaction mixture was stirred for an additional 50 minutes. It was then diluted with EtOAc (700 mL) and washed with 1 N HCl solution (230 mL, 2×), and brine. The organic layer was dried with MgSO$_4$, filtered and evaporated in vacuo to afford an oil containing yellow precipitate.

The crude material was directly submitted to silica gel flash chromatography. The column was first flushed with 25% EtOAc/hexanes, then eluted first with 75:25:0.5:0.5 hexanes/ EtOAc/MeOH/90% formic acid, followed by 75:25:0.5:0.5 EtOAc/ hexanes/MeOH/90% formic acid. Two fractions of the desired material were collected: a slightly impure fraction 12 as a white foam (2.46 g), and a pure hydroxy acid 12 as an off-white dense solid (19.5 g; a two step combined yield of >67%).

Optical purity analysis of acid 12 with HPLC: Acid 12 was converted to its methyl ester according to the procedure described for IA, with the exception that 10% EtOAc/hexanes was employed in the flash chromatography purification. Analysis of the resulting colorless oil according to the conditions noted below gave ~94% ee.

Chiral HPLC Analysis
Instrument: HP 1090 Liquid Chromatography with DAD
Column: Chiracel OD, 0.46 cm×25 cm
Mobile Phase: 95:5 hexanes/IPA
Flow Rate: 1.0 mL/min
Detection: UV absorption @ 210 nm
Sample was prepared in 1:1 hexanes/IPA
Elution time: 6.92 min (S-hydroxy methyl ester); 8.73 min (R-hydroxy methyl ester)

Optical purity enhancement of hydroxy acid 12 via recrystallization: Several batches of hydroxy acid 12 with an ee in the range of 93–94%, and a total weight of 57.0 g were mixed and ground up with a mortar and pestle. The material was divided into two equal batches, and each was dissolved in 140 mL EtOAc at room temperature, treated with 280 mL hexanes, and then stored in a refrigerator for 21 hours. The precipitate was filtered and washed with 100 mL of 10% EtOAc/hexanes and air dried. The two sets afforded a total of 23.3 g of white fluffy solid. Chiral HPLC analysis of its methyl ester derivative indicated an ee >99.5%.

A second crop gave 7.3 g; chiral HPLC analysis indicated an ee >99.5%), and a third crop gave 8.3 g with an ee of 99.4%.

12: MP 145.0–147.5° C. IR (KBr): 3433, 3389, 2959, 2922, 2857, 1739, 1728. $^1$H NMR (CDCl$_3$, d=7.28): 7.38 (d, J=1.9, 1H, C-1 H), 7.33 (d, J=8.2, 1H, C-4H), 7.20 (dd, J=8.2, 1.9, 1H, C-3H), 5.23 (s, 1H, C$\underline{H}$OH), 1.70 (app s, 4H, CH$_2$CH$_2$),1.30 (s, 3H, CH$_3$),1.29 (s, 3H, CH$_3$), 1.28 (s, 6H, CH$_3$/CH$_3$). LRMS (ESI) m/z (M–H)$^-$=261.4.

Anal. Calcd. for C$_{16}$H$_{22}$O$_3$: C, 73.25; H, 8.45 Found: C, 73.47; H, 8.34.

$[\alpha]^{25}$D=–100.85° (c, 1.016, MeOH).

J. (R)-3-Fluoro-4(2'(5",6",7",8"-tetrahydro-5",5",8",8"-tetramethyl-2"-naphthyl)2'-hydroxy)acetamido benzoic acid, 1(2-propenyl) ester, 7a A THF (50.0 mL) solution of trichloromethyl chloroformate (12.0 mL, 99.5 mmol) was added dropwise over 4 minutes to a THF (200.0 mL) solution of hydroxy acid 12 (26.2 g, 99.9 mmol). The solution was heated with an oil bath (63–65° C.) for 5 hours and 10 minutes. The oil bath was replaced with a water bath of 35° C., and the reaction mixture was flushed with N$_2$ for 1.5 hours. Most of the left-over volatile component of the reaction mixture was removed in vacuo, and the resulting crude oil was exposed to high vacuum for 1 hour with intermittent N$_2$ flushing. The crude was diluted with CH$_2$Cl$_2$ and evaporated. The resulting oil was exposed to high vacuum for 45 minutes with intermittent N$_2$ flushing to give 12a.

Aniline 3 (17.7g, 90.7 mmol) was added to a CH$_2$Cl$_2$ (195.0 mL) solution of crude dioxolanedione (12a) over a few minutes. The reaction mixture was stirred for a total of 16 hours. It was diluted with CH$_2$Cl$_2$ (450 mL) and washed with water (220 mL). The CH$_2$Cl$_2$ layer was dried with MgSO$_4$, filtered and evaporated in vacuo. The crude material was then purified with repeated flash chromatography (silica gel; CH$_2$Cl$_2$ elution to afford a mixture of aniline 12 and alcohol 7a, followed by 20% EtOAc elution to afford clean alcohol 7a). The material from the CH$_2$Cl$_2$ elution was resubmitted to the same condition to afford more clean coupled material. A white foam (33.7 g, 77% yield) was obtained. ee >99.5%.

7a: IR (KBr): 3442 (br), 3374, 2961, 2928, 2861, 1724, 1699, 1620, 1594, 1527. $^1$H NMR (CDCl$_3$, δ=7.28): 8.77 (br d, J=2.8, 1H, NH), 8.51 (app t, J=8.1, FCCCH), 7.87 (d, J=9.2, 1H, FCCH), 7.80 (dd, J=11.4, 1.8, 1H, CHCH$\underline{H}$CO$_2$), 7.42 (d, J=1.9, 1H, CC$\underline{H}$CCOH, 7.36 (d, J=8.2, CC$\underline{H}$CHCCOH), 7.25 (dd, J=8.2, 1.9, CCHC$\underline{H}$CCOH), 6.02 (m, 1H, OCH$_2$C$\underline{H}$), 5.42 (dm, J=17.2, 1H, =CH$_2$ trans), 5.32 (dm, J=10.4, 1H, =CH$_2$ cis), 5.24 (d, J=2.5, 1H, C$\underline{H}$OH), 4.83 (dm, J=5.7, 2H, OCH$_2$), 3.11 (d, J=2.5, 1H, CHO$\underline{H}$), 1.70 (s, 4H, CH$_2$CH$_2$),1.33 (s, 3H, CH$_3$), 1.30 (s, 3H, CH$_3$),1.29 (s, 6H, CH$_3$/CH$_3$). LRMS (ESI) m/z (M–H)$^-$=438.5.

Anal. Calcd. for C$_{26}$H$_{30}$FNO$_4$: C, 71.05; H, 6.88; N, 3.19. Found: C, 70.79; H, 6.87; N, 3.14.

$[\alpha]^D_{25}$=+2.50 (c, 1.898, MeOH).

K. (R)-3-Fluoro-4(2'(5",6",7",8"-tetrahydro-5",5",8",8"-tetramethyl-2"-naphthyl)2'-hydroxy)acetamido benzoic acid, (R) IA Pd(Ph$_3$P)$_4$ (0.55 g, 0.476 mmol) was added to a THF (190.0 mL) solution of allyl benzoate 7a (20.55 g, 46.76 mmol) and morpholine (29.0 mL, 332.5 mmol). The reaction mixture was stirred for 20 minutes. It was diluted with EtOAc (300.0 mL) and washed with 1N HCl (170.0 mL, 2×) and brine, and dried with MgSO$_4$. The mixture was filtered and evaporated in vacuo. Purification with flash chromatography (sample was loaded as a silica gel mesh; 75:25:0.5:0.5 hexanes/EtOAc/MeOH/90% formic acid→60:40:0.5:0.5 EtOAc/hexanes/MeOH/90% formic acid) afforded acid (R) IA as an off-white solid. The acid was dissolved in EtOAc (58 mL) with heating; then were added hot hexanes (470 mL) during one minute. The solution was cooled and the precipitate was filtered and washed with 100 mL of 20% EtOAc/hexanes. Acid (R) IA was retrieved as a white shiny solid (16.4 g, 87.8% yield).

(R) IA: Mp=194.5–199.0° C. IR (KBr) 3565, 3421, 3396, 3068, 2957, 2924, 2904, 2856, 1721, 1685, 1676, 1618, 1592, 1526. $^1$H NMR (DMSO, δ=2.51) 13.12(s, CO$_2$H), 9.79 (d, J=1.5, NH), 8.10 (app t, J=8.3, NHCC$\underline{H}$), 7.78–7.72 (m, 2H, FCC$\underline{H}$CC$\underline{H}$), 7.46 (d, J=1.5, CCHC), 7.30 (d, J=8.1, 1H, CHC$\underline{H}$CCOH), 7.21 (dd, J=8.1, 1.5, 1H, CHC$\underline{H}$CCOH), 6.58 (d, J=4.5, 1H, OH), 5.16 (d, J=4.5, CHO$\underline{H}$), 1.63 (s, 4H, CH$_2$CH$_2$),1.25 (s, 3H, CH$_3$),1.24 (s, 3H, CH$_3$), 1.22 (s, 6H, CH$_3$/CH$_3$). LRMS (ESI) m/z (M–H)$^-$=398.5.

Anal. Calcd. for C$_{23}$H$_{26}$FNO$_4$: C, 69.19; H, 6.56; N, 3.51. Found: C, 69.23; H, 6.37; N, 3.44.

$[\alpha]^D_{25}$=+1.13 (c, 2.113, MeOH). Chiral HPLC analysis of the methyl ester derivative: ee >99.5%.

Biology

The transactivation assay measures the ability of a retinoid to activate a reporter gene in the presence of one of the retinoic acid receptor subtypes ($\alpha$, $\beta$, or $\gamma$). The details of the receptor-based transactivation assay are disclosed in the literature, e.g. see Nature 1988, 332, 850–853. In the retinoid transactivation assay, HeLa cells are co-transfected with DNA encoding RAR $\alpha$,$\beta$or $\gamma$, and an RAR responsive CAT (chloramphenicol acetyl transferase) reporter gene. Retinoid efficacy is measured by the concentration of induced CAT gene product as determined by ELISA assay. The dosage at which CAT level is ½ the maximum level is termed the $EC_{50}$. The mean $EC_{50}$ value for each of the receptors is calculated using a computer generated induced-fit program. The following table reports the $EC_{50}$ values for both enantiomers (in nM):

| | Transactivation $ED_{50}$ (% max) | | |
| --- | --- | --- | --- |
| Compound | RAR-$\alpha$ | RAR-$\beta$ | RAR-$\gamma$ |
| (R) I | NA | 300 (86) | 20 (98) |
| Racemate | NA | 400 (31) | 30 (80) |
| (S) I | NA | NA | NA |

All the activity resides in the R enantiomer.

Non-receptor-selective retinoids have been shown to prevent the conversion of papillomas to malignant tumors in the two-stage system of mouse skin carcinogenesis, where DMBA (7,12-dimethyl-benzanthracene) is used as the initiator and 12-tetradecanoyl-phorbol-13 acetate (TPA) is used as the promoter. The model and results are described in, for example, L. C. Chen, et al.; *Cancer Letters*, 78, pp. 63–7 (1994); D. R. Shalinsky, et al., *Proc. Ann. Meet. Am. Assoc. Cancer Res.*, 35, p. A-831 (1994); and L. C. Chen, et al.; *Carcinogenesis*, 15, pp. 2383–6 (1994). They have also been shown to be of benefit in human organ transplant patients, who are at increased risk of developing malignant skin tumors due to the required immunosuppressive therapy. Clinical studies are described in S. Euvrard, et al., *BioDrugs*, 8, pp. 176–84 (1997); J. N. B. Bavinck, et al., *J. Clin. Oncol.*, 13, pp.1933–8 (1995); and G. E. Gibson, et al., *J. Eur.Acad. Dermatol. Venereol.*, 10, pp. 42–7 (1998). The present inventors have now discovered that the active, enantiomer IA possesses superior activity in this model.

The model used was essentially the same as described in the references above. Compound IA and 13-cis-retinoic acid (control) were given to several groups of mice by intraperitoneal injection at the start of the TPA promotion phase, and the number and size of papillomas were monitored for 10 weeks. Compound IA at doses of 15 mg/kg or higher signficiantly reduced both the number and size of papillomas, while 13-cis-retinoic acid at 50 mg/kg was inactive under these conditions. The results of the study are summarized in the table below:

| Treatment | Tumor Incidence (% of mice with tumors) | Tumor Burden, mm$^3$ (mean tumor size per mouse) |
| --- | --- | --- |
| IA (5 mg/kg) | 70 | 7.0 |
| IA (15 mg/kg) | 45 | 1.2* |
| IA (30 mg/kg) | 15 | 0.8* |
| 13-cis-retinoic acid | 80 | 6.8 |
| Vehicle | 90 | 6.6 |
| Untreated | 90 | 6.8 |

*statistically significant difference ($p < 0.05$) vs. vehicle or untreated

We claim:

1. A method for the prevention of spontaneous squamous cell carcinoma in immunocompromised human transplant patients which comprises systemically administering a therapeutically effective amount of a compound of the formula

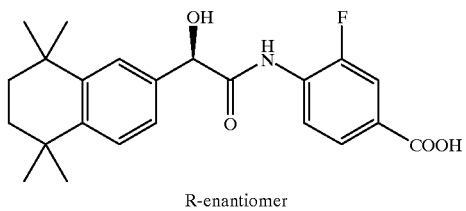

R-enantiomer or a pharmaceutically acceptable salt thereof.

* * * * *